(12) United States Patent
Blair et al.

(10) Patent No.: US 7,898,420 B2
(45) Date of Patent: Mar. 1, 2011

(54) TRANSPONDER HOUSING AND DEVICE TO MARK IMPLEMENTS, SUCH AS SURGICAL IMPLEMENTS, AND METHOD OF USING SAME

(75) Inventors: William A. Blair, San Diego, CA (US); Bruce E. Barnes, Escondido, CA (US); David A. Poirier, Escondido, CA (US)

(73) Assignee: RF Surgical Systems, Inc., Bellevue, WA (US)

( * ) Notice: Subject to any disclaimer, the term of this patent is extended or adjusted under 35 U.S.C. 154(b) by 99 days.

(21) Appl. No.: 12/046,396

(22) Filed: Mar. 11, 2008

(65) Prior Publication Data
US 2008/0238677 A1 Oct. 2, 2008

Related U.S. Application Data

(60) Provisional application No. 60/894,435, filed on Mar. 12, 2007.

(51) Int. Cl.
*G08B 13/14* (2006.01)
(52) U.S. Cl. .................................. 340/572.1; 340/572.9
(58) Field of Classification Search ............... 340/572.1, 340/572.9
See application file for complete search history.

(56) References Cited

U.S. PATENT DOCUMENTS

| 4,114,601 | A |   | 9/1978  | Abels .......................... 128/1 R |
|-----------|---|---|---------|------------------------------------------|
| 4,193,405 | A |   | 3/1980  | Abels .......................... 128/296 |
| 5,057,095 | A | * | 10/1991 | Fabian ........................ 604/362  |
| 5,107,862 | A |   | 4/1992  | Fabian et al. ................. 128/899  |
| 5,188,126 | A |   | 2/1993  | Fabian et al. ................. 128/899  |
| 5,224,593 | A | * | 7/1993  | Bennett ....................... 206/5.1  |
| 5,329,944 | A |   | 7/1994  | Fabian et al. ................. 128/899  |
| 5,456,718 | A |   | 10/1995 | Szymaitis ...................... 623/11  |
| 5,629,498 | A |   | 5/1997  | Pollock et al. .................. 177/15 |
| 5,664,582 | A |   | 9/1997  | Szymaitis .................... 128/898   |
| 5,923,001 | A |   | 7/1999  | Morris et al. .................. 177/245 |
| 5,931,824 | A |   | 8/1999  | Stewart et al. ................. 604/358 |
| 5,969,613 | A | * | 10/1999 | Yeager et al. .............. 340/572.9   |
| 6,026,818 | A |   | 2/2000  | Blair et al. .................... 128/899 |
| 6,276,033 | B1| * | 8/2001  | Johnson et al. .............. 24/704.1   |
| 6,366,206 | B1|   | 4/2002  | Ishikawa et al. ........... 340/573.1    |

(Continued)

FOREIGN PATENT DOCUMENTS
WO 2006/060781 A1 6/2006

OTHER PUBLICATIONS

U.S. Appl. No. 60/811,376, filed Jun. 6, 2006, Blair et al.

(Continued)

*Primary Examiner* — Daniel Wu
*Assistant Examiner* — John F Mortell
(74) *Attorney, Agent, or Firm* — Seed IP Law Group PLLC

(57) ABSTRACT

A transponder device and/or housing to mark a surgical implement, such as a metallic surgical instrument, is provided that comprises a non-elastic, preferably non-metallic, rigid transponder housing attachable to a portion of the surgical implement. The housing includes a transponder receiving cavity spaced at least 1 millimeter, and preferably at least 2 millimeters, from any portion of the surgical implement when the housing is attached to the surgical implement. The housing may be removably attached to the surgical implement or permanently attached. In use, a transponder is installed in the transponder receiving cavity. A method of detecting a transponder indicating the possible presence of a surgical implement is also provided.

27 Claims, 12 Drawing Sheets

U.S. PATENT DOCUMENTS

| | | | | |
|---|---|---|---|---|
| 6,734,795 | B2 | 5/2004 | Price | 340/572.1 |
| D502,419 | S | 3/2005 | Copen | D10/104 |
| 6,861,954 | B2 | 3/2005 | Levin | 340/572.1 |
| 6,998,541 | B2 | 2/2006 | Morris et al. | 177/15 |
| 7,019,650 | B2 | 3/2006 | Volpi et al. | 340/572.1 |
| D526,586 | S | 8/2006 | McCaghren et al. | D10/65 |
| 7,118,029 | B2 | 10/2006 | Nycz et al. | 235/375 |
| 7,135,973 | B2 | 11/2006 | Kittel et al. | 340/568.2 |
| 7,135,978 | B2 | 11/2006 | Gisselberg et al. | 340/572.5 |
| 7,142,118 | B2 | 11/2006 | Hamilton et al. | 340/572.1 |
| D534,448 | S | 1/2007 | Shaffer, II et al. | D10/104 |
| 7,158,754 | B2 | 1/2007 | Anderson | 455/41.1 |
| 7,183,914 | B2 | 2/2007 | Norman et al. | 340/568.1 |
| 7,183,927 | B2 | 2/2007 | Kolton et al. | 340/572.8 |
| 7,307,530 | B2 | 12/2007 | Fabian et al. | 340/572.1 |
| D568,186 | S | 5/2008 | Blair et al. | D10/70 |
| 2002/0070863 | A1* | 6/2002 | Brooking | 340/572.1 |
| 2003/0105394 | A1 | 6/2003 | Fabian et al. | 600/407 |
| 2004/0129279 | A1 | 7/2004 | Fabian et al. | 128/899 |
| 2004/0250819 | A1 | 12/2004 | Blair et al. | 128/899 |
| 2004/0254420 | A1 | 12/2004 | Ward | 600/37 |
| 2005/0049564 | A1 | 3/2005 | Fabian | 604/362 |
| 2005/0131397 | A1 | 6/2005 | Levin | 606/1 |
| 2006/0084934 | A1 | 4/2006 | Frank | 604/362 |
| 2006/0106368 | A1 | 5/2006 | Miller et al. | 606/1 |
| 2006/0202827 | A1 | 9/2006 | Volpi et al. | 340/572.1 |
| 2007/0034670 | A1 | 2/2007 | Racenet et al. | 227/180.1 |
| 2007/0038233 | A1 | 2/2007 | Martinez et al. | 606/157 |
| 2007/0055109 | A1 | 3/2007 | Bass et al. | 600/234 |

OTHER PUBLICATIONS

U.S. Appl. No. 60/892,208, filed Feb. 28, 2007, Blair et al.

* cited by examiner

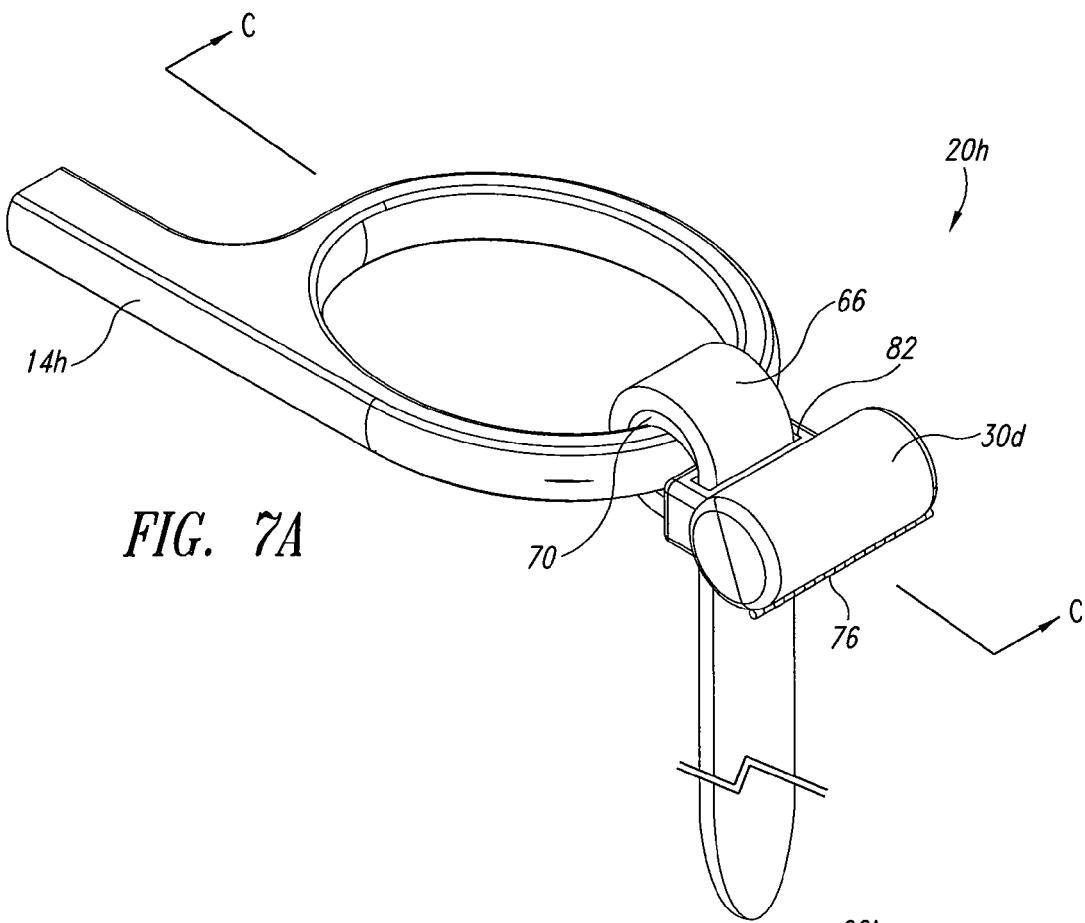
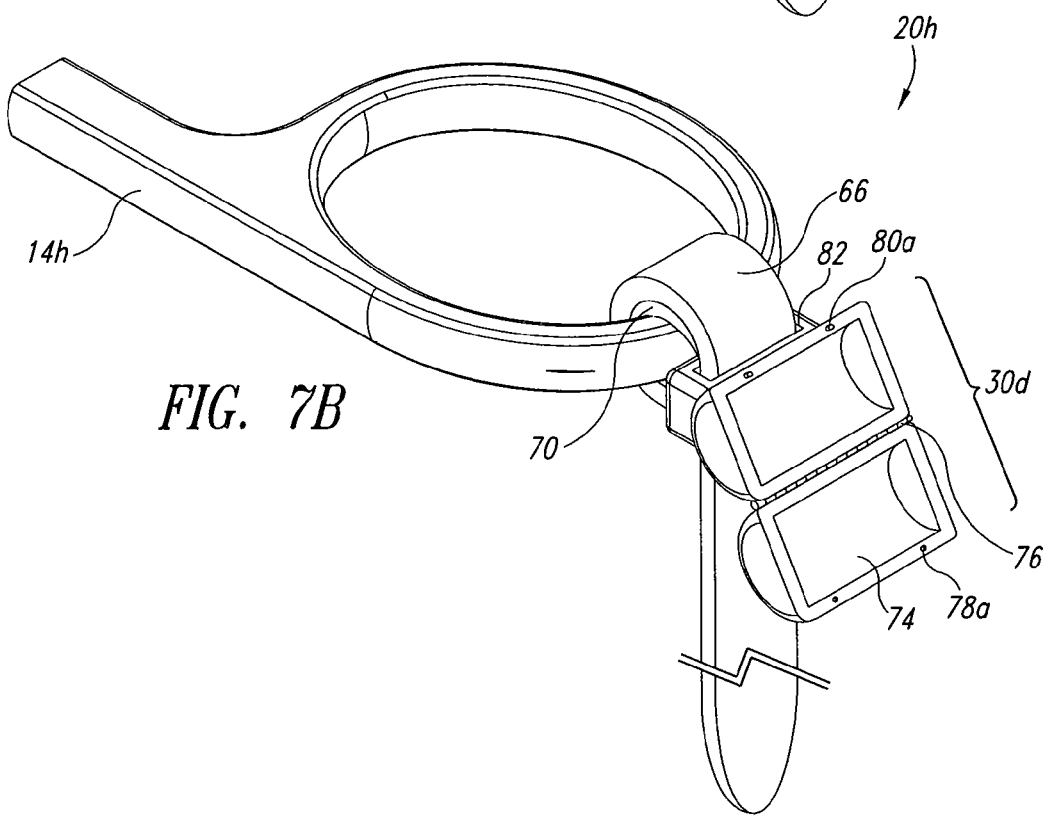

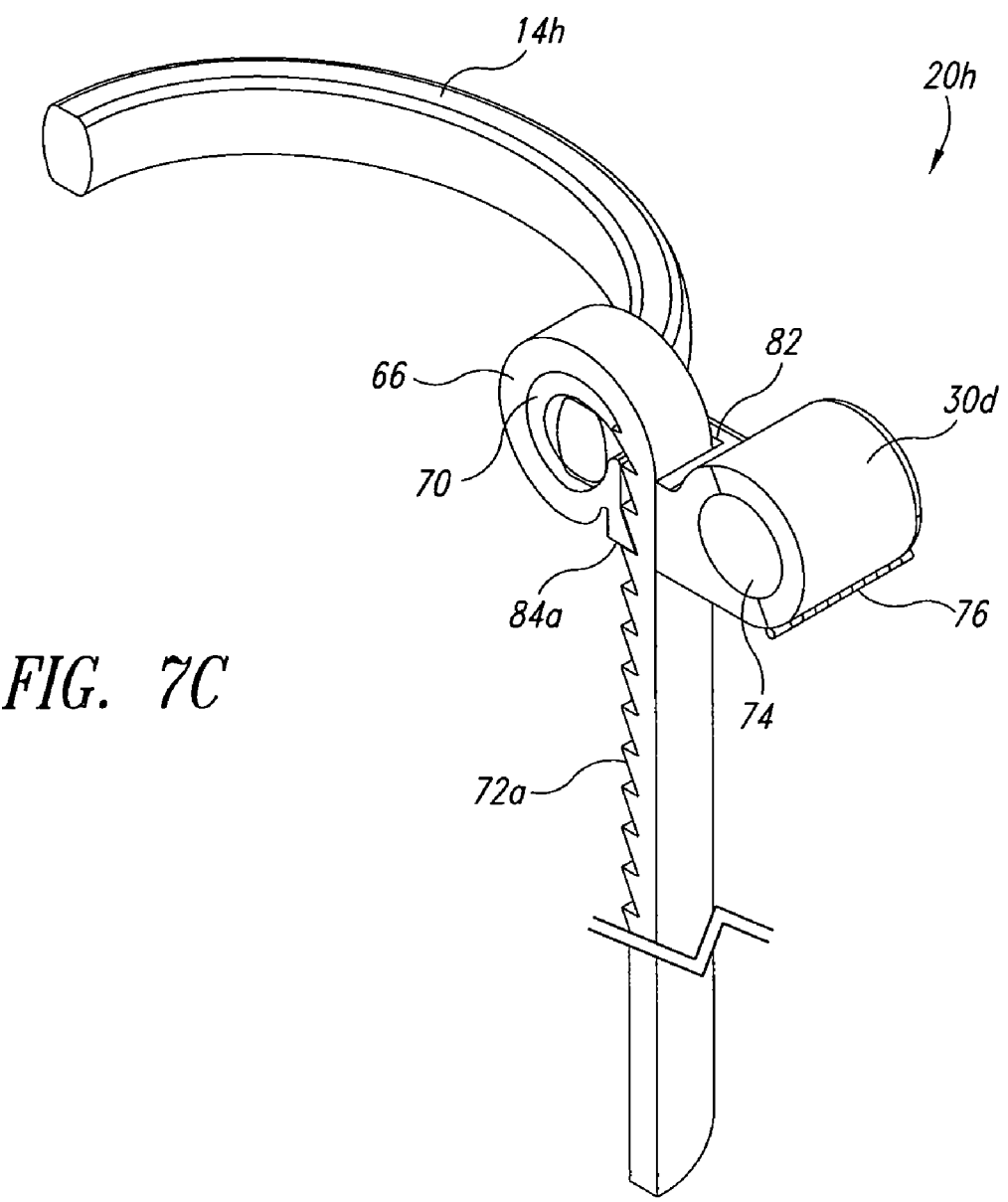

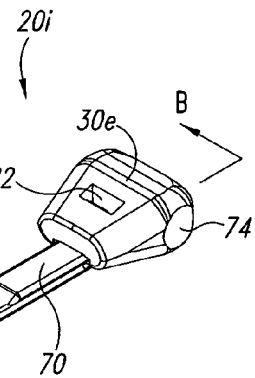
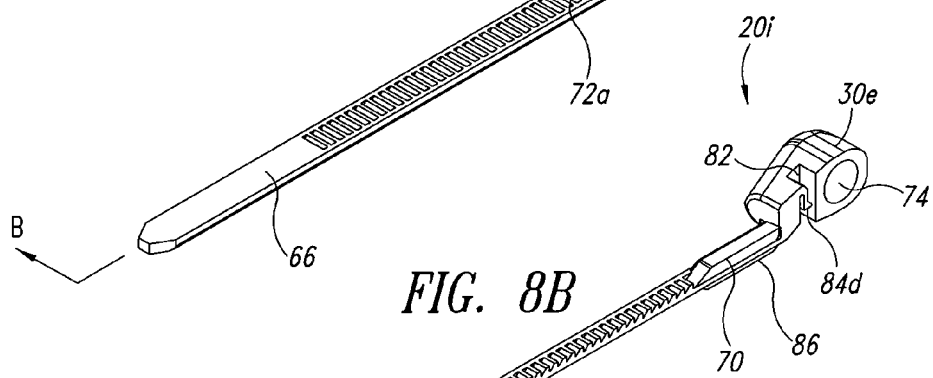
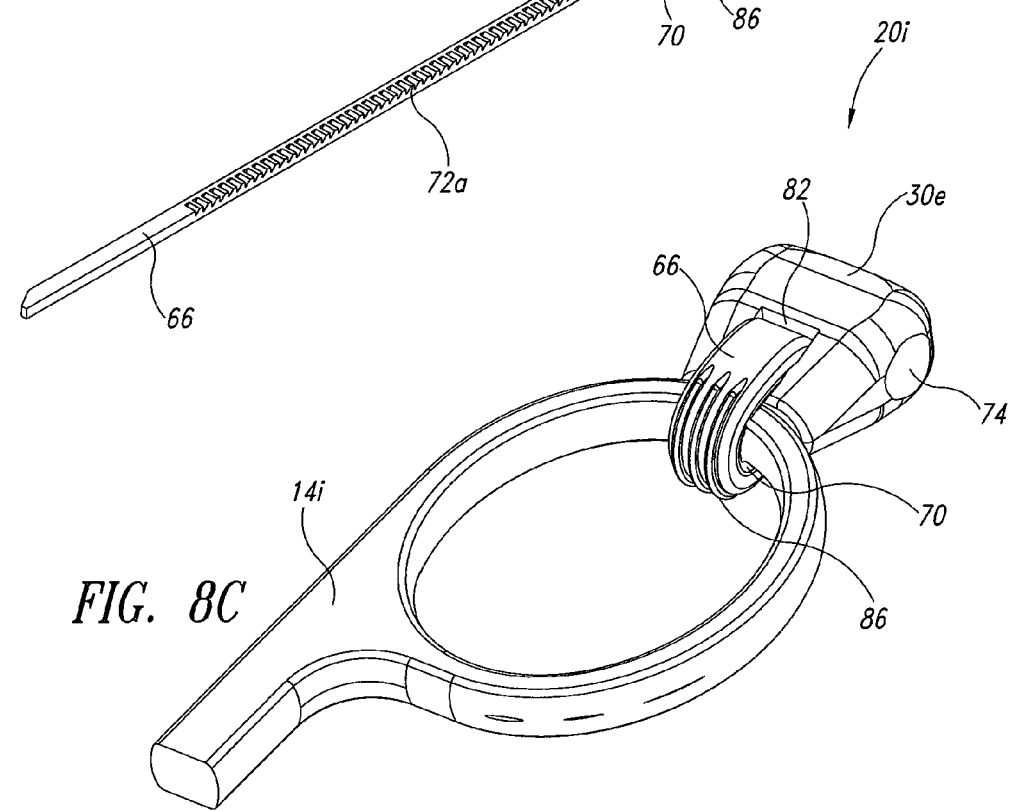

TRANSPONDER HOUSING AND DEVICE TO MARK IMPLEMENTS, SUCH AS SURGICAL IMPLEMENTS, AND METHOD OF USING SAME

CROSS-REFERENCE TO RELATED APPLICATION

This application claims the benefit under 35 U.S.C. §119(e) of U.S. Provisional Patent Application No. 60/894,435 filed Mar. 12, 2007, which is incorporated herein by reference in its entirety.

BACKGROUND

1. Technical Field

This disclosure generally relates to a device for marking rigid implements, such as surgical instruments.

2. Description of the Related Art

It is often useful or important to be able to determine the presence or absence of a foreign object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures, which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system may include a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost effective and highly accurate. In particular, false negatives must be avoided to ensure that objects are not mistakenly left in the patient. The overall automated system requires a large number of transponders, since at least one transponder is carried, attached or otherwise coupled to each object which may or will be used in surgery. Consequently, the transponders and devices for carrying, attaching or coupling the transponder to the object should be inexpensive. However, such inexpensive devices may hinder accurate detection. For instance, if the object and/or the device carrying the transponder is metallic or other metallic objects are present in the body, a transponder that is in fact present may not be able to be detected as a result of the metallic object acting as a Faraday shield or otherwise interfering with transponder communications. The transponder and/or device should be capable of undergoing sterilization. Consequently, a new inexpensive device, for carrying, attaching, or coupling a transponder to a surgical implement is highly desirable.

BRIEF SUMMARY

At least one embodiment may be summarized as a device to mark surgical implements, including a non-elastic rigid housing attachable to a portion of a surgical implement, the housing including a shell having an implement receiving cavity sized to receive at least a portion of the surgical implement and a transponder receiving cavity sized to receive a transponder, the transponder receiving cavity spaced at least about 1 millimeter from any portion of the surgical implement when the housing is attached to the surgical implement.

The device to mark surgical implements may further include the transponder, wherein the transponder is removably retained in the transponder receiving cavity. The housing may be removably attachable to the portion of the surgical implement.

The device to mark surgical implements may further include a detent mechanism that is integral to the housing to attach the housing to the portion of the surgical implement. The implement receiving cavity may be an asymmetric passage. The transponder receiving cavity may be at least two millimeters from any portion of the surgical implement when the housing is attached to the surgical implement. The shell of the housing may have a first portion and a second portion, and a coupling structure adapted to connect the first and the second portions together. The coupling structure may be a snap. The coupling structure may be a clip. The first and the second portions of the shell of the housing may be connected by a hinge. The hinge may be integral with the first and the second portions. The housing may be composed of plastic, the plastic able to withstand multiple sterilizations in an autoclave. The housing may be non-metallic.

At least one embodiment may be summarized as a device to mark surgical implements, including a flexible strap, the strap able to encircle at least a portion of a surgical implement; and a housing having a strap receiving cavity sized to receive at least a portion of the strap to retain the strap to the housing and a transponder receiving cavity sized to receive a transponder, the transponder receiving cavity spaced at least about 1 millimeter from any portion of the surgical implement when the housing is attached to the surgical implement via the strap.

The device to mark surgical implements may further include the transponder, wherein the transponder is removably retained in the transponder receiving cavity. The strap may have a first end and a second end, the first end secures to the second end to form a loop, the loop encircling at least a portion of the surgical implement. The housing may include a securing structure to secure the strap within the strap receiving cavity. The securing structure may fixedly secure the strap within the strap receiving cavity. The securing structure may removably secure the strap within the strap receiving cavity. The securing structure may be a detent mechanism. The detent mechanism may include a pawl formed integrally in the slot receiving cavity and the strap may include a number of teeth adapted to engage the pawl. The strap may be a material different from the material of the housing. The transponder receiving cavity may be at least two millimeters from any portion of the surgical implement when the housing is attached to the surgical implement via the strap. The housing may have a first portion and a second portion, and a coupling structure adapted to connect the first and the second portions together. The coupling structure may be at least one of a snap or a clip. The first and the second portions of the housing may be connected by a hinge. The strap and the housing may be integral. The housing may be composed of plastic, the plastic able to withstand multiple sterilizations in an autoclave. The housing may be non-metallic.

At least one embodiment may be summarized as a transponder device including a housing having at least two distinct pieces, the housing removably attachable to a portion of a surgical implement; coupling means for coupling the at least two distinct pieces together to form a transponder receiving cavity therebetween; and a wireless transponder received in the transponder receiving cavity. At least one of the pieces of the housing may be non-elastic. At least one of the pieces of the housing may be non-metallic. The housing may position the wireless transponder at least 1 millimeter from the surgical implement when attached to the portion of the surgical implement. The housing may position the wireless transponder at least 2 millimeters from the surgical implement when coupled to the surgical implement. At least one piece of the housing may be made of plastic, the plastic able to withstand multiple sterilizations in an autoclave. The housing may have a cavity sized to receive at least a portion of the surgical implement.

The transponder device may further include a detent mechanism that is integral to the housing to attach the housing to the portion of the surgical implement. The housing may form an asymmetric passage to receive the portion of the surgical implement.

At least one embodiment may be summarized as a surgical instrument including instrument means; a handle connected to the instrument means; a non-elastic non-metallic housing removably attached to at least a portion of the handle, the housing having a two-piece body coupled together by coupling means to form a transponder receiving cavity therebetween; and a wireless transponder enclosed within the transponder receiving cavity of the housing wherein the housing positions the wireless transponder at least 1 millimeter from the handle. The instrument means may be at least one of a cutting means, a grasping means, a clamping means, an access means, an injection/irrigation means, or a measurement means. The coupling means may be at least one of a snap, a strap, or a clip. The housing may position the wireless transponder approximately 2 millimeters from the at least a portion of the handle. The housing may have an integral detent mechanism to attach the housing to at least the portion of the handle. The instrument means may be metallic.

At least one embodiment may be summarized as a method including attaching a non-elastic rigid non-metallic housing having an implement receiving cavity onto a portion of each of one or more rigid surgical implements, the housing positioning a wireless transponder enclosed within the housing at least 1 millimeter from the portion of the surgical implement; transmitting a signal in a first frequency band during a first time proximate to a confined area; transmitting a signal in a second frequency band during a second time proximate to the confined area; receiving a response, if any, to the transmission of the signal in the first frequency band; and receiving a response, if any, to the transmission of the signal in the second frequency band. Attaching a non-elastic rigid non-metallic housing onto a portion of each of one or more rigid surgical implements may include removably attaching the housing onto the portion of the surgical implements. Attaching a non-elastic rigid non-metallic housing onto a portion of each of one or more rigid surgical implements may include attaching two parts of the housing together using a coupling structure. Attaching a non-elastic rigid non-metallic housing onto a portion of each of one or more rigid surgical implements may include actuating a detent mechanism of the housing.

The method may further include before transmitting the signal in the first frequency band, using at least one of the one or more surgical implements to perform a surgical task. Attaching a non-elastic rigid non-metallic housing onto a portion of each of one or more rigid surgical implements may include positioning the transponder at least 2 millimeters from the surgical implement.

The method may further include sterilizing at least one of the one or more surgical implements by autoclaving the at least one surgical implement with the housing still attached to the surgical implement.

At least one embodiment may be summarized as a method including attaching a non-elastic rigid non-metallic housing having a strap receiving cavity onto a portion of each of one or more rigid surgical implements via a flexible strap, the housing positioning a wireless transponder enclosed within the housing at least 1 millimeter from the portion of the surgical implement; transmitting a signal in a first frequency band during a first time proximate to a confined area; transmitting a signal in a second frequency band during a second time proximate to the confined area; receiving a response, if any, to the transmission of the signal in the first frequency band; and receiving a response, if any, to the transmission of the signal in the second frequency band. Attaching a non-elastic rigid non-metallic housing having a strap receiving cavity onto a portion of each of one or more rigid surgical implements via a strap may include securely attaching the housing onto the portion of each of one or more surgical implements by pulling the strap through the strap receiving cavity such that the strap actuates a detent mechanism of the housing.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 7A is an isometric view of a transponder device having a transponder housing secured to a portion of a surgical implement according to still another illustrated embodiment.

FIG. 7B is an isometric view of the transponder housing of FIG. 7A with the transponder housing in an open position to access a transponder receiving cavity therein.

FIG. 7C is a cross-sectional view of the transponder device of FIG. 7A.

FIG. 8A is an isometric view of a transponder device having a transponder housing according to a further illustrated embodiment.

FIG. 8B is a cross-sectional view of the transponder device of FIG. 8A.

FIG. 8C is a isometric view of the transponder device of FIG. 8A attached to a portion of a surgical implement.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers, and types of surgical instruments have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a surgical environment will be used as an example environment for detecting implements but such should not be considered limiting.

Figure 1:
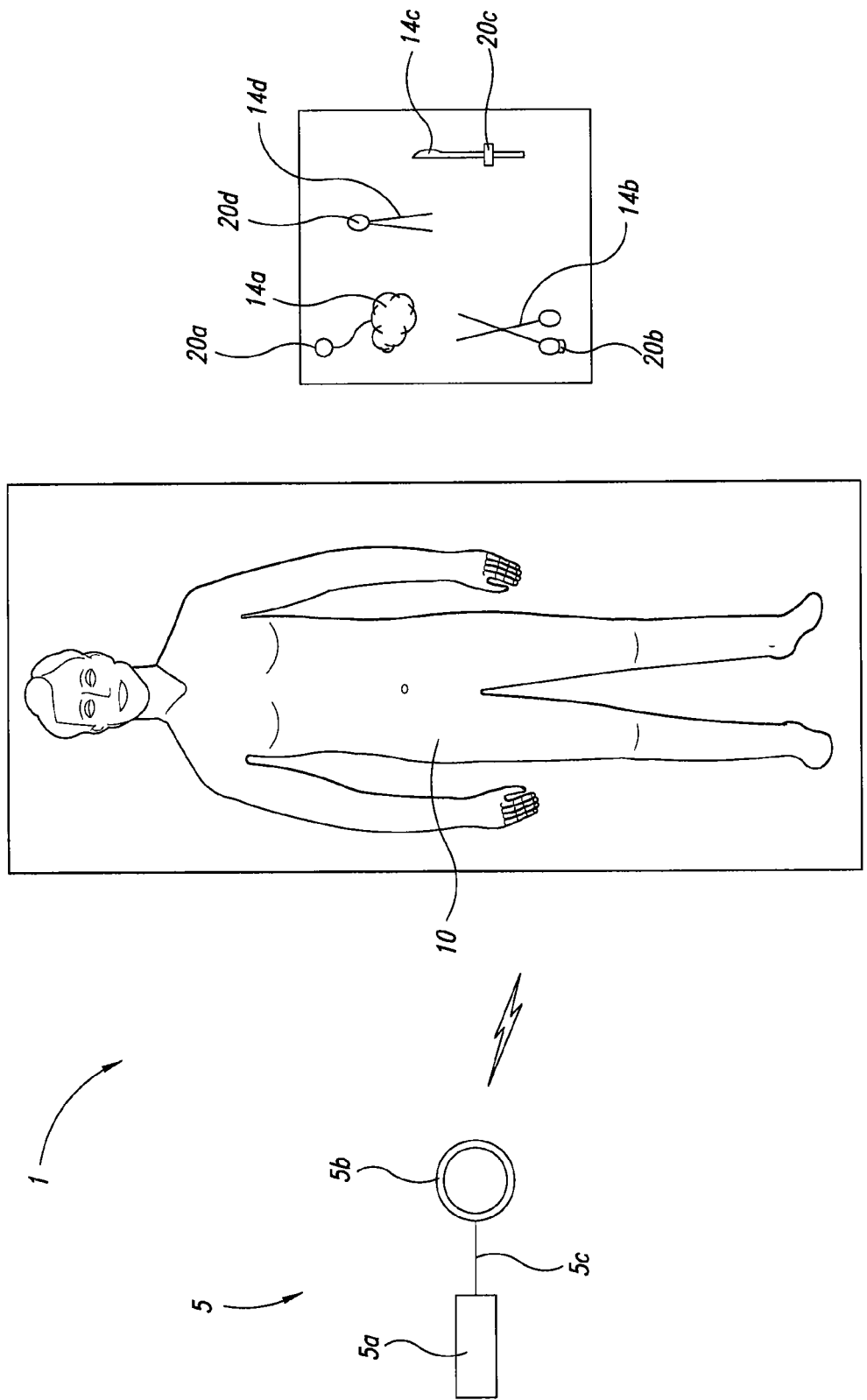
FIG. 1 is a schematic diagram showing a surgical environment illustrating use of an interrogation and detection system to detect one or more objects tagged with a transponder in a patient, according to one illustrated embodiment.

FIG. 1 shows a surgical environment 1 in which a medical provider (not shown) operates an interrogation and detection system 5 to ascertain the presence or absence of objects in, or on, a patient 10.

The interrogation and detection system 5 may include a controller 5a and an antenna 5b. The antenna 5b is coupled to the controller 5a by one or more communication paths, for example a coaxial cable 5c. The antenna 5b may take the form of a hand-held wand. The controller 5a is configured to cause the antenna to emit wireless interrogation signals in one or more wide frequency bands, to receive responses from transponders to such interrogation signals, and to determine the presence or absence of a transponder based on the received responses, if any.

The surgical environment 1 may include a number of surgical implements, collectively 14. Surgical implements 14 may take a variety of forms, for example instruments, accessories and/or disposable objects useful in performing surgical procedures. Each surgical implement 14 is tagged with a transponder device, collectively 20. Thus, surgical implements 14a-14d may each be tagged with a respective transponder device 20a-20d.

The transponder device 20 includes a transponder 38 (FIGS. 3 and 4B) and a transponder housing, collectively 30 (FIGS. 2, 3, 5A-B, 6A-B, 7A-D, 8A-C, 9A-B and 10) that attaches or couples the surgical implement 14. The transponder housing 30 carries the transponder 38 and spaces the transponder 38 from any metallic portion of the surgical implement 14 such that the surgical implement 14 does not interfere with wireless communications between the transponder 38 and the antenna 5b of the interrogation and detection system 5.

In some embodiments, the transponder 38 is received in the transponder housing 30. The transponder 38 is typically small, for example approximately 5-10 millimeters long with a diameter of about 1-4 millimeters. In addition, in at least some embodiments, the transponder housing 30 advantageously protects the transponder from the ambient environment, for instance from forces, pressure and/or fluids, such as body fluids.

Embodiments of the transponder device 14 disclosed herein are particularly suited to operate with metallic implements. As used in this specification and the appended claims, a metallic implement, such as surgical implements, may be made partially or wholly of metal, so long as the implement could act, alone or in association with other metallic objects, as a Faraday shield or otherwise interfere with communications between the transponders 38 and the interrogation and detection system 5. Examples of various types of metallic implements include, but are not limited to, cutting means (e.g., a scalpel 20c, lancet, knife, scissors), grasping means (e.g., tweezers 14d, forceps), clamping means (e.g., hemostat 14b, clamps), access means (e.g., dilators, specula), injection/irrigation means (e.g., needles, tips), drilling means (e.g., a drill bit), or measurement means (e.g., rulers, calipers). In addition, to the metallic surgical implements, other surgical implements may also be tagged and identified for use with the interrogation and detection system, such as a sponge 14a. In some embodiments, some or all of those surgical implements are tagged using other types of transponder devices or attachment structures.

In use, the medical provider (not shown) may position the antenna 5b proximate the patient 10 in order to detect the presence or absence of the transponder 38 and hence a foreign metallic object. The medical professional may in some embodiments move the antenna 5b along and/or across the body of the patient 10. In some embodiments, the antenna 5b may be sized to fit at least partially in a body cavity of the patient 10. Different types of transponders 38 may be used in the various transponder housings 30. Although a human patient 10 is illustrated, the described interrogation and detection system 1 may similarly be used on animals.

Figure 2:
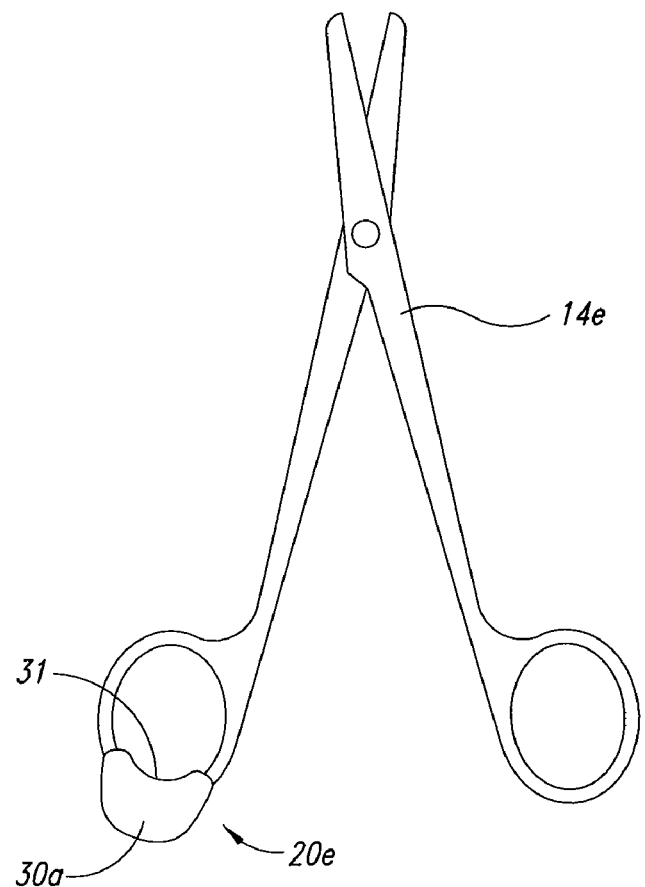
FIG. 2 is a front elevational view of a surgical implement with a transponder device attached according to one embodiment.

FIG. 2 illustrates a transponder device 20e attached to a surgical implement 14e, according to one embodiment.

The transponder device 20e is advantageously attached to a portion of a handle of a surgical implement 14e such that the transponder device 20e does not physically interfere with the operation of the surgical implement 14e. The transponder device 20e includes a transponder housing 30a. The transponder housing 30a may include one or more structures to accommodate a user's (e.g., surgeon or assistant) fingers or other body parts, such as the arcuate or concave finger receiving structure 31. The transponder housing 30a may also be designed and configured to couple to a portion of the surgical implement 14e such that the transponder housing 30a does not intervene between or interfere with movement of adjacent structures of the surgical implement 14e. For example, the transponder housing 30a may be positioned on the surgical implement 14e to allow the finger hole portions of the surgical implement 14e to be moved into immediate adjacent positions with respect to one another.

Figure 3:
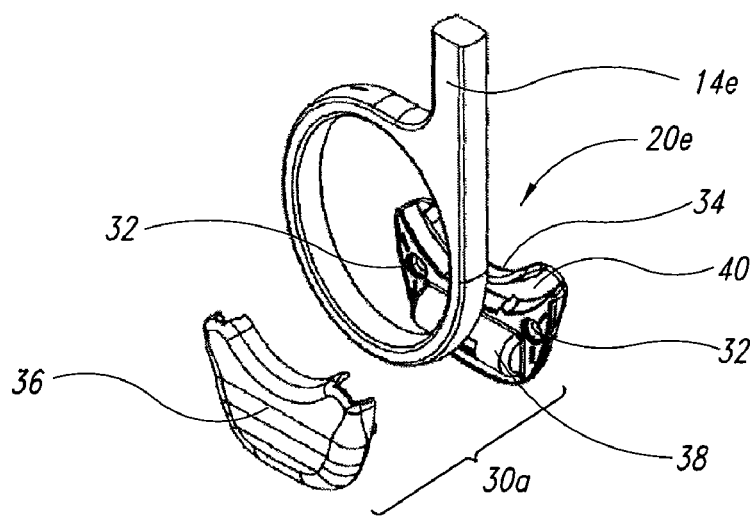
FIG. 3 is an isometric view showing two portions of a transponder housing positioned to receive a portion of a surgical instrument therebetween, and a transponder received in the transponder housing according to one embodiment.

FIG. 3 is an isometric view of the transponder device 20e showing the two-piece transponder housing 30a in further detail.

In this illustrated embodiment, the transponder device 20e includes a housing 30a formed from two body portions 34, 36 which carry a transponder 38. The body portions 34, 36 form a surgical implement receiving cavity 40 that is sized, dimensioned and otherwise configured to receive a portion of the handle of the surgical implement 14e. In at least some embodiments, the two body portions are attached by a hinge (not shown). The hinge may be attached directly to the two body portions or formed integrally therewith, and may be made of flexible material or rigid moving components.

The two body portions 34, 36 form a shell that is coupled together using body portion coupling means. For example, the two body portions 34, 36 may be coupled together via snap means, for instance snaps 42 (FIG. 4A) received by holes 32. Although two snaps 42 are illustrated, more snaps may be used in some embodiments. Other coupling structures may also be utilized, such as clamping structures or clamps, clipping structures or clips, detent structures or detents, and/or mechanical fasteners (e.g., screws, straps). Such mechanical fasteners may advantageously be non-metallic fasteners, for example plastic or nylon. In some embodiments, the coupling means may allow for uncoupling. Such embodiments may need significant force (e.g., over 80 pounds) to separate the body portions 34, 36 in order to prevent the transponder housing 30a from falling off the surgical implement 14e during an operation, sterilization, or other use. For similar reasons, in some embodiments, the transponder housing 30 contains a detent mechanism (e.g., to prevent the transponder housing 30 from changing location during use). In at least some embodiments, a tool may be needed to separate a two-piece body of the housing.

The transponder 38 may be constructed in various manners. For example, the transponder 38 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. Additional details about types of transponders may be found in U.S. Provisional Patent Application No. 60/811,376 filed Jun. 6, 2006 and U.S. Provisional Patent Application Ser. No. 60/892,208, filed Feb. 28, 2007.

Figure 4A:
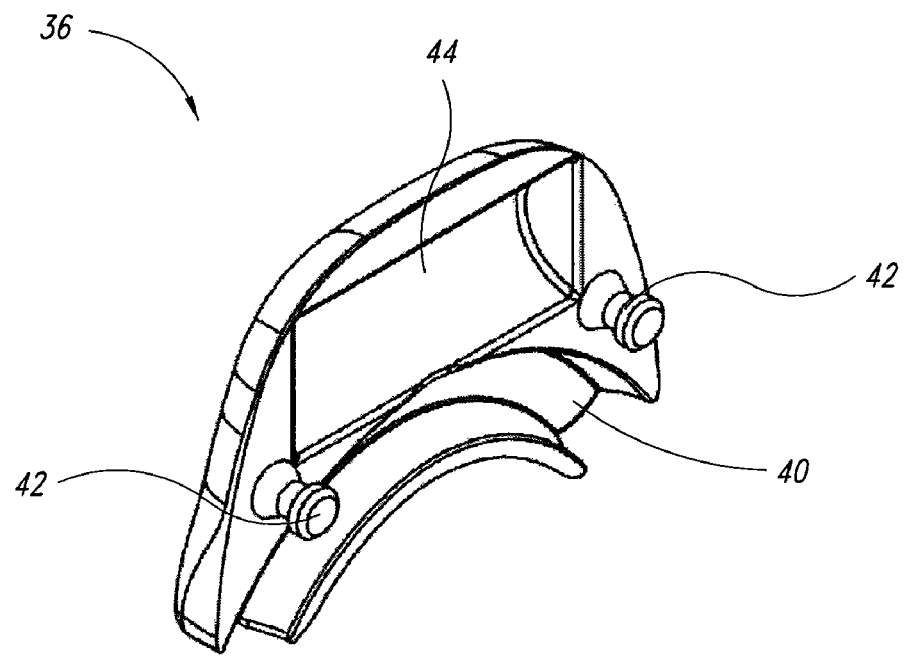
FIGS. 4A-4B are enlarged isometric views of each piece of the transponder housing illustrated in FIG. 3.
Figure 4B:
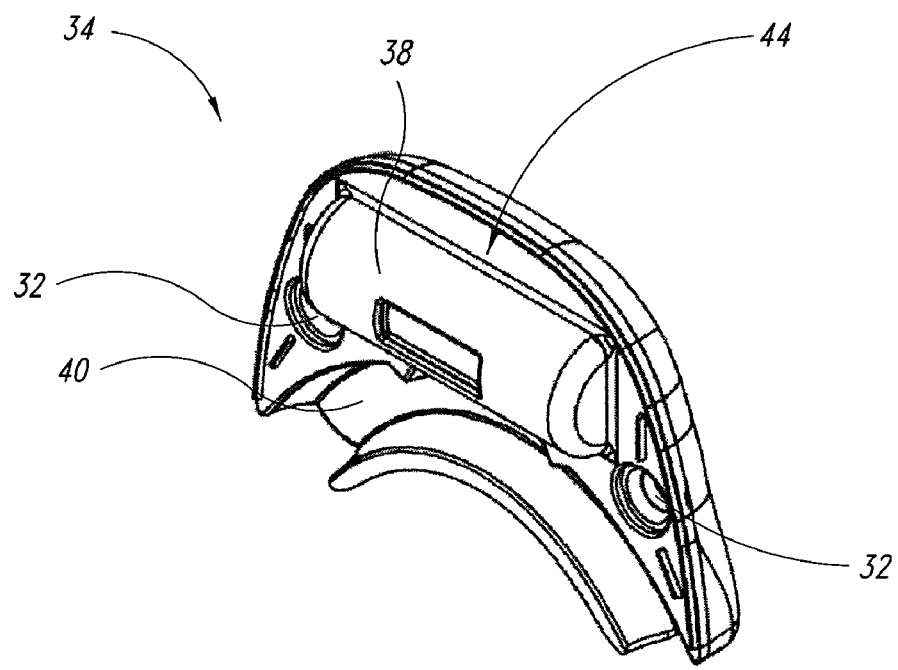

FIGS. 4A-4B are enlarged isometric views of each body portion 34, 36 of the transponder device 20e illustrated in FIG. 3.

The male body portion 36 illustrated in FIG. 4A contains two snaps 42, a pre-formed or pre-existing transponder receiving cavity 44, and the surgical implement receiving cavity 40. The snaps 42 hold the two body portions 34, 36 together when inserted into the holes 32 of the female piece 34. The transponder receiving cavity 44 spaces the transponder 38 at least about 1 millimeter and preferably at least about 2 millimeters from any metallic portion of the surgical implement 14e when the transponder housing 30a is attached or otherwise coupled to the surgical implement 14e. Advantageously, if the surgical implement 14e is metallic, the distance helps to prevent signal loss due to the metallic implement acting as a Faraday shield or otherwise interfering with wireless communications of the transponder 38. The transponder receiving cavity 44 may be asymmetrically positioned with respect to an outer perimeter (e.g., as best illustrated in FIG. 2) of the transponder housing 30e, to achieve the desired separation of the transponder 38 from the surgical implement 14e in a reduced or minimal form factor or package.

At the transponder receiving cavity 44, the transponder housing 30a may hold the transponder 38 in place by coupling means. For example, the transponder receiving cavity 44 may include a receptacle or cavity sized to receive at least a portion of the transponder 38. In some embodiments, the receptacle or cavity may be sized to snuggly receive at least a portion of the transponder 38, for example with a friction or interference fit. For example, in some embodiments, the transponder 38 may be glued in the transponder receiving cavity 44. In at least some embodiments, the transponder housing 30 forms an implement receiving cavity 40 that is an asymmetric passage, sized and shaped to receive a particular size and shape of a portion of a surgical implement 14. The transponder receiving cavity 44 may be pre-formed or pre-existing, that is the transponder receiving cavity 44 may exist independent of the presence or existence of a transponder 38. Thus, the housing 30a may be produced or manufactured separately from the transponder 38, which may later be loaded into the transponder receiving cavity 44, and possibly subsequently removed therefrom.

FIG. 4B illustrates the female body portion 34 of the transponder housing 30a. In the illustrated embodiment, the female body portion 34 has a complimentary surgical implement receiving cavity 40, holes 32, and a transponder receiving cavity 44 to receive or otherwise carry the transponder 38. The surgical implement-receiving cavity 44 is sized and shaped to receive a portion of a surgical implement 14.

Figure 5A:
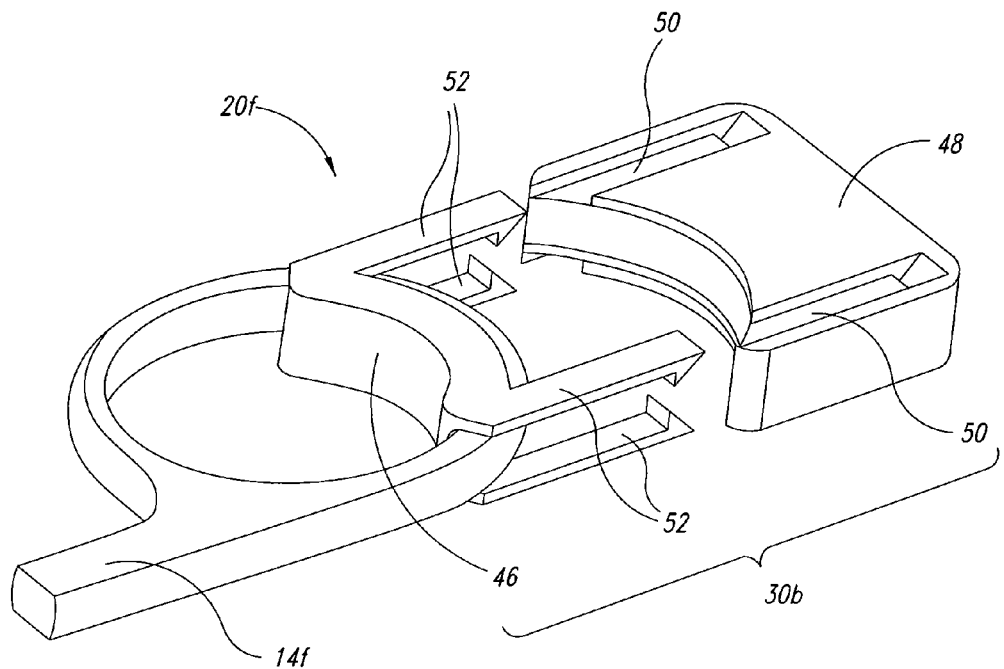
FIG. 5A is an isometric view showing two portions of a housing positioned to receive a portion of a handle of a surgical implement therebetween according to another illustrated embodiment.

FIG. 5A illustrates an alternative transponder device 20f attaching to a portion of a handle of a surgical implement 14f.

Figure 5B:
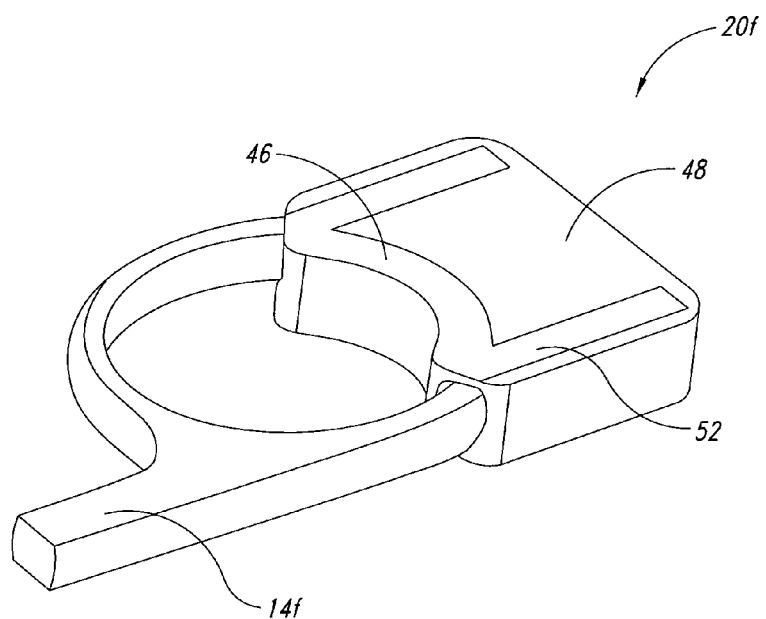
FIG. 5B is an isometric view showing the two portions of the transponder housing of FIG. 5A with the handle of the surgical implement secured therebetween.

The illustrated embodiment includes a two-piece transponder housing 30b including both male and female body portions 46, 48, respectively. The male piece 46 has multiple elongated members 52 with hooked ends, that fit into complementary cavities 50 on the female piece 48. Although four elongated members are illustrated, more or less members may be used in other embodiments. The elongated members are resilient and act as clips, which couple together the body portions 46, 48. The transponder (not shown) in this illustrated embodiment is located inside the female piece 48. FIG. 5B illustrates the transponder device 20f of FIG. 5A attached to the handle of the surgical implement 14f.

Figure 6A:
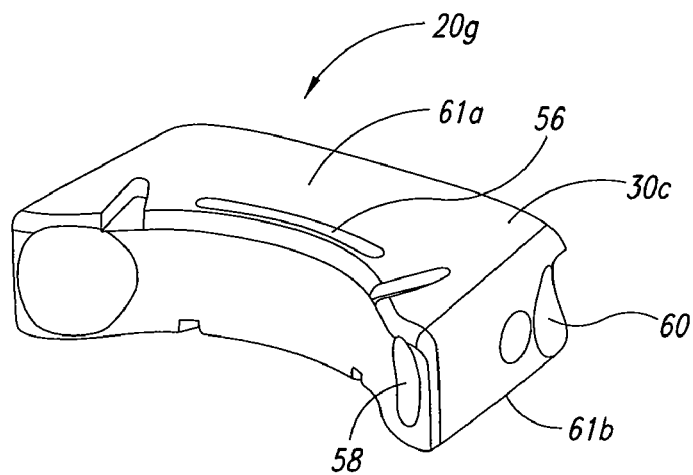
FIG. 6A is an isometric view of a transponder device having a transponder housing according to yet another illustrated embodiment.

FIG. 6A shows a transponder device 20g according to yet another illustrated embodiment.

In the illustrated embodiment, the transponder housing 30c advantageously has multiple surgical implement receiving receptacles 58 and 60 so the same transponder housing 30c may be used on various differently shaped surgical implements 14. A first portion of housing 30c (e.g., upper portion 61a) may be hinged or separable from a second portion of the housing (e.g., lower portion 61b) to move from a closed position (illustrated in FIG. 6A) to an open position (not illustrated) in order to place a portion of the surgical implement 14 in the implement receiving receptacles 58 and 60 of transponder housing 30c. The first portion of the housing 30c may then be moved to the closed position to fasten the surgical implement in the implement receiving receptacle 58, 60. The first and second portions of the transponder housing 30c may have or carry complimentary coupling structures to secure the portions together, for example, snaps, pins, detents, fasteners, etc.

Figure 6B:
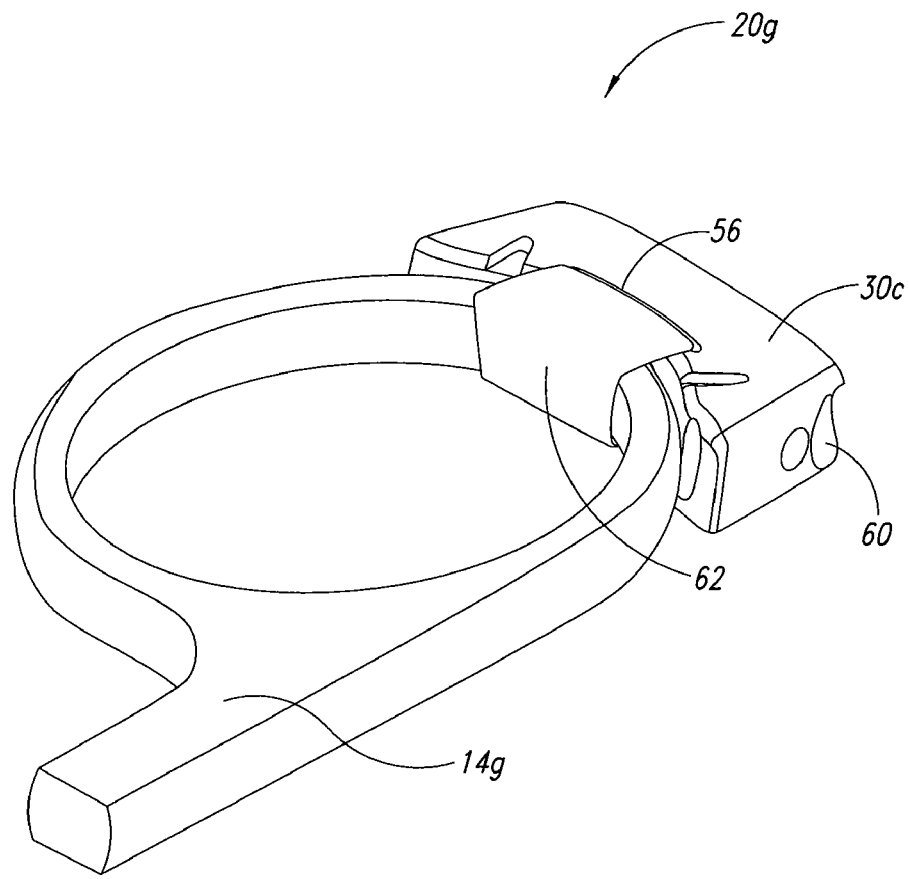
FIG. 6B is an isometric view of the transponder housing of FIG. 6A secured to a portion of a surgical implement via a strap.

The transponder housing 30c may further have a strap receiving slot 56 so the same transponder housing 30c may be used on other various differently shaped surgical implements 14. In such an embodiment, instead of placing a portion of the surgical instrument in the surgical implement receiving receptacles 58, 60, a portion of the surgical implement 14g is instead placed proximate to the transponder housing 30c. In some cases, this is desirable to maintain the ergonomic design of the handle of the surgical implement 14g. FIG. 6B illustrates such an embodiment. The transponder device 20g attaches to a portion of a surgical implement 14g by way of a strap 62 inserted through strap receiving slot 56. The transponder housing 30c may include securing structures to fixedly or removably secure the strap 62 within the strap receiving slot 56. Such structures may, for example, include one or more detent mechanisms. Alternatively, the strap 62 may be secured to itself, for example to form a closed loop structure. In some embodiments the strap 62 may be made of a different material (e.g., metal, fabric) from the rest of the transponder housing 30c and may in some embodiments be disposable. Straps may be of varying length and may be trimmed flush with the transponder housing after attachment. In some embodiments which employ a strap 62, the transponder housing 30c may be a single unitary piece.

FIG. 7A shows a transponder device 20h according to yet another illustrated embodiment.

In the illustrated embodiment, the transponder housing 30d has an integral flexible strap 66 that is able to encircle a portion of a surgical implement 14h to attach the transponder device 20h to the surgical implement 14h. The strap 66 may be selectively tightened around the portion of the surgical implement 14h by passing the strap 66 through a strap receiving slot 82 and applying a tensile force to the end of the strap 66. The transponder device 20h optionally includes a resilient material 70 on at least a portion of the strap 66 to facilitate attachment to surgical instruments of varying sizes and shapes. Resilient material 70 may be additionally placed on a second portion of the strap 66 to protect a user's hand from abrading on the strap material when using a surgical implement with the transponder device 20h attached. Resilient material 70 is preferably made out of thermoplastic elastomers but can be any resilient material.

Figure 7D:
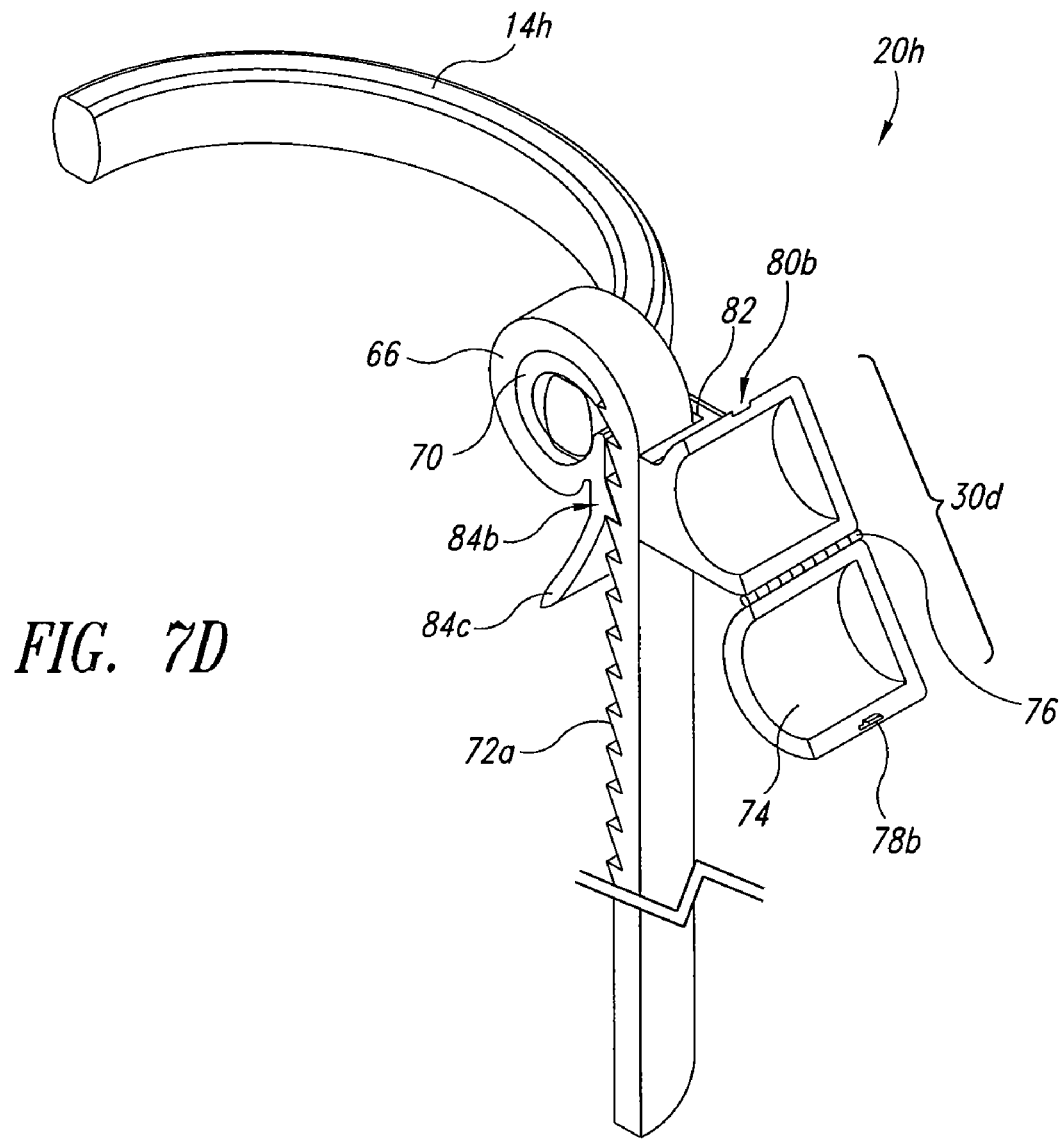
FIG. 7D is a cross-sectional view of an alternate embodiment of the transponder device of FIG. 7A.

The transponder housing 30d may be a single unitary piece or have two separate portions with complimentary coupling structures to secure the portions together, for example, snaps, pins, detents, fasteners, etc. The transponder housing 30d may further comprise a hinge 76 connecting the portions together, thus allowing the portions to move from a closed position or configuration (FIG. 7A) to an open position or configuration (FIG. 7B) in order to place or remove a transponder 38 (not shown) in or from a transponder receiving cavity 74. While the hinge 76 is illustrated as a barrel and pin, other forms of hinges may be employed, for example a single web of a pliable material where the two portions are formed as a single unitary piece, for example by injection molding. FIG. 7B illustrates the transponder device 20h in the open position or configuration, revealing holes 78a and snaps 80a for coupling portions of the transponder housing 30d together. FIG. 7C is a sectional view of the transponder device 20h of FIGS. 7A and 7B. The transponder housing 30d includes a securing structure 84 to retain the strap 66 to the transponder housing 30d. In the illustrated embodiment, the securing structure is a detent mechanism formed of a pawl 84a that engages teeth 72a of the strap 66 when the strap 66 is received in the strap receiving cavity 82. The strap 66 may be fixedly or removably secured to the transponder housing 30d. FIG. 7D is a cross-sectional view of an alternate embodiment of the transponder housing 30d wherein pawl 84b has an extended feature or lever 84c to allow a user to release strap 66 from a secured position within the transponder housing 30d. In the illustrated embodiment, portions of the transponder housing 30d are secured together by one or more resilient clips 78b and complimentary cavities 80b.

FIGS. 8A-8C show a transponder device 20i according to yet another illustrated embodiment.

In the illustrated embodiment, the transponder housing 30e has an integral flexible strap 66 having teeth 72a that is able to encircle a portion of a surgical implement 14i and engage pawl 84d to attach the transponder housing 30e to the surgical implement 14i. The transponder housing 30e has a transponder receiving cavity 74 in which a transponder 38 (not shown) may be removably placed. The transponder 38 may be secured in the housing 30e by friction or interference fit. A first portion of strap 66 may include a first resilient material 70 to facilitate the attachment of the transponder device 20i to surgical instruments of varying sizes. A second portion of strap 66 may include a second resilient material 86 to protect a user's hand from abrasion when using a surgical instrument 14i with the transponder device 20i attached. The first resilient material 70 may be the same or a different material than the second resilient material 86.

Figure 9A:
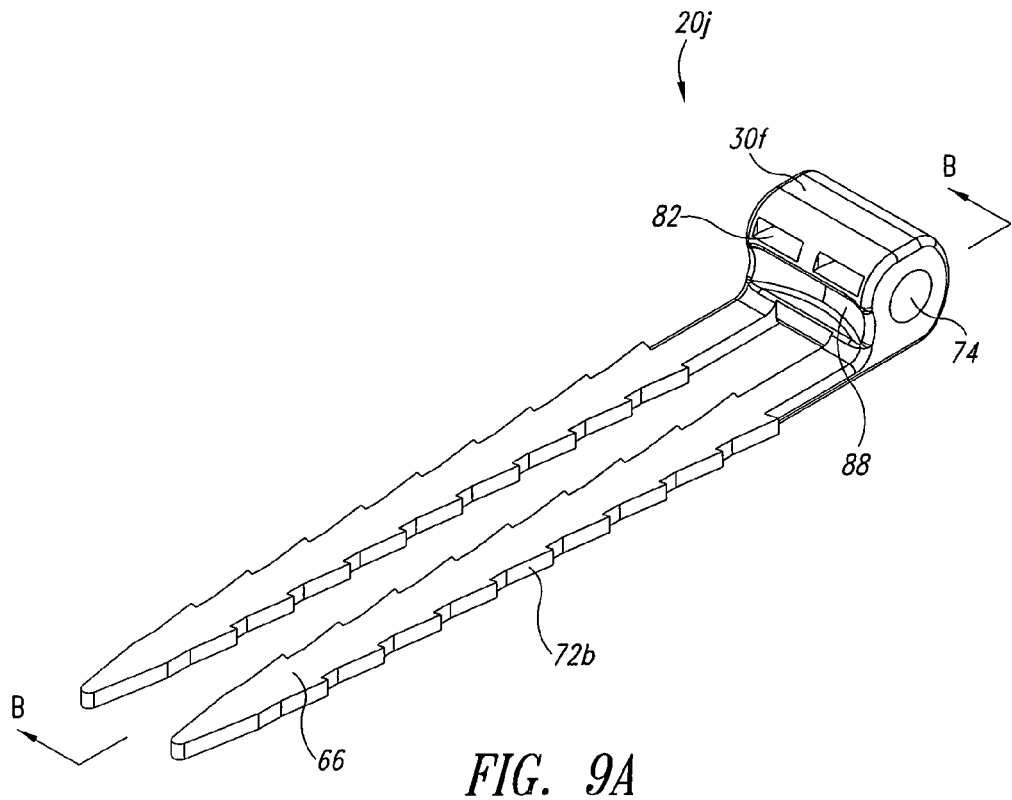
FIG. 9A is an isometric view a transponder device having a transponder housing according to still a further illustrated embodiment.
Figure 9B:
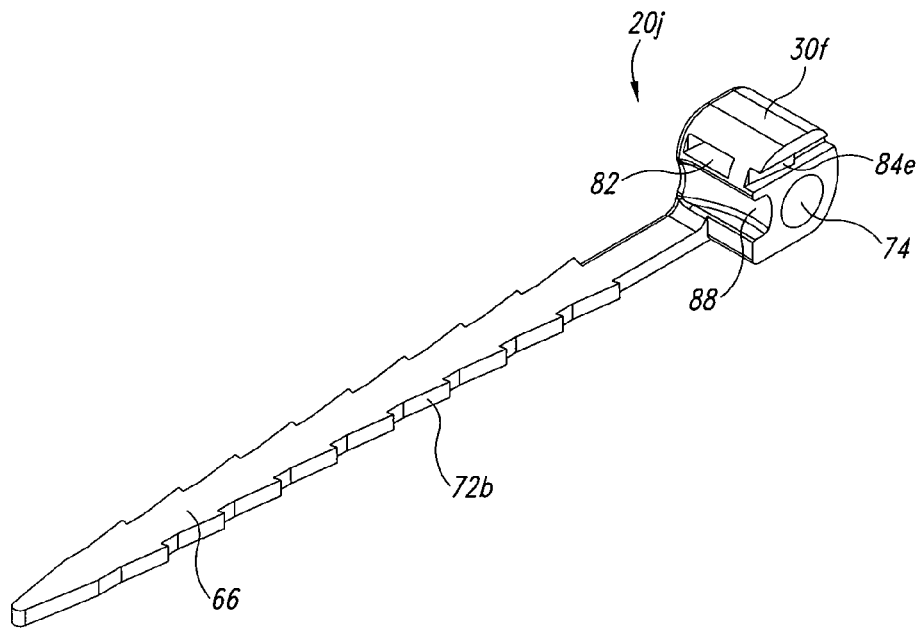
FIG. 9B is a cross-sectional view of the transponder device of FIG. 9A.

FIGS. 9A and 9B show a transponder device 20j according to yet another illustrated embodiment.

In the illustrated embodiment, the transponder housing 30e has a plurality of flexible straps 66 that are able to encircle a portion of a surgical implement 14 (not shown) and engage securing structure 84e of the transponder housing 30f via teeth 72b located on the straps 66. Transponder housing 30e may further have a contour structure 88 sized and shaped to receiving a complementary contour of a surgical implement. A transponder receiving cavity 74 is provided to receive a transponder 38 (not shown) and space the transponder from the surgical instrument when attached thereto.

Figure 10:
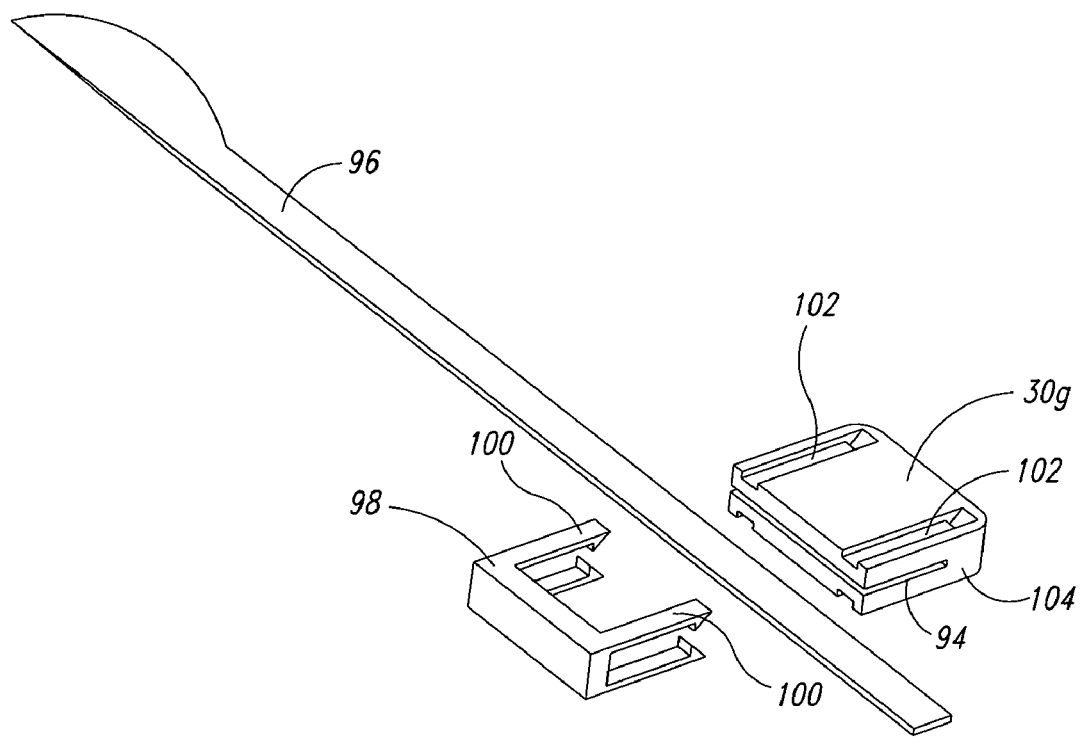
FIG. 10 is an isometric view of a scalpel with a transponder device being attached according to one illustrated embodiment.

The size and shape of the transponder housing 30 may be adapted to attach onto various portion of surgical implements. For example, FIG. 10 illustrates a transponder housing 30g being attached to a straight edge of handle of a scalpel 96. The scalpel 96 fits in the surgical implement-receiving cavity 94, which is a rectangular slot. The illustrated two-piece transponder housing 30g is similar to the one illustrated in FIG. 5A. The illustrated transponder housing 30g has a male piece 98 with four elongated members 100 that fit within the complimentary cavities 102 on the female piece 104. The elongated members 100 are resilient and act as clips to couple the male and female pieces 98, 104 together. In other embodiments, a transponder housing 30 for a drill bit may be cylindrical and formed in order to prevent an imbalance in weight that prevents normal operation of the drill bit.

A non-elastic rigid transponder housing 30 ensures that the transponder 38 is appropriately spaced from the surgical implement 14 without regard to the orientation (e.g., with respect to gravity) of the surgical implement 14 and/or without regard to forces or pressures that may be asserted on or through the surgical implement 14 and/or transponder housing 30. Various materials may be used to make a non-elastic, rigid, preferably non-metallic, transponder housing 30, for example various plastics, nylons or glasses. Since it is advantageous to reuse the transponder housing 30 to reduce costs, it is desirable to make the transponder housing 30 out of a material that is able to withstand multiple sterilizations, such as by autoclaving the transponder housing 30 or exposing the transponder housing 30 to ultraviolet (UV) light. Such sterilizations may occur in some embodiments with the transponder housing 30 still attached to the surgical implement 14. For example, the transponder housing 30 may be made out of bio-inert, high service temperature plastic, such as those made under the trade names KRATON G® or PROFAX® polypropylene homopolymer.

In some embodiments, transponder devices 20 may be permanently attached to the surgical implements 14. In other embodiments, the transponder devices 20 are removably attachable to the surgical implements 14. Advantageously, transponder devices 20 that are removably attachable may allow the transponder devices 20 to be moved between various surgical implements 14. For example, such may allow transponder devices 20 to be used on new implements 14 after older implements 14 are disposed or while older implements 14 are being refurbished (e.g., sharpened). In some embodiments, the surgical implements 14 may be provided to the end user (e.g., hospital, surgeon or other medical services provider) with the transponder device 20 attached. In other embodiments, the end user may attach or couple the transponder devices 20 to the surgical implements 14, and/or may remove the transponder devices 20 from the surgical implements 14. Such may allow a manufacturer, distributor or end user to produce and/or stock one set of surgical implements 14 which may be customized with an appropriate transponder based on the particular needs or system of the end user.

Figure 11:
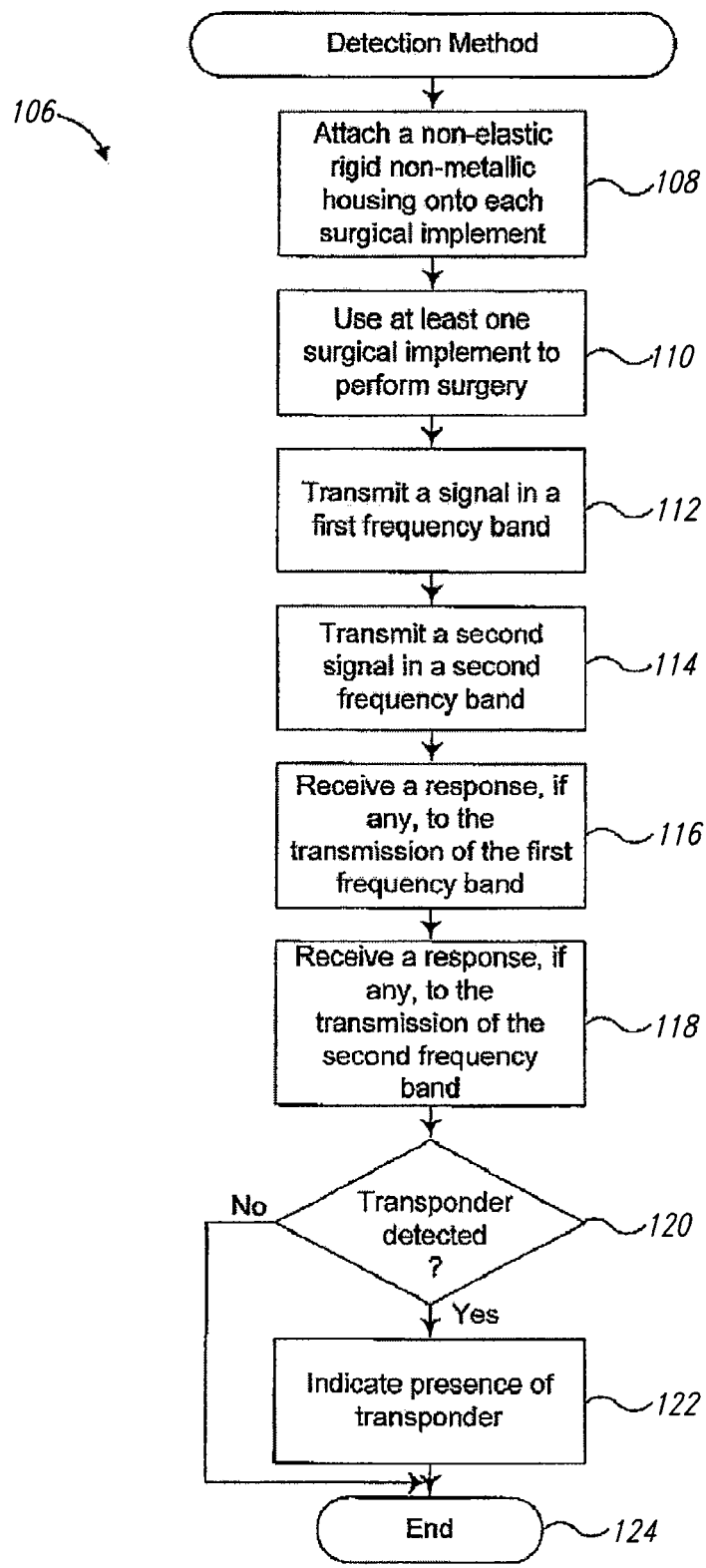
FIG. 11 is a flow diagram of a method for detecting the presence of a foreign object according to one illustrated embodiment.

FIG. 11 is a flow diagram of a method 106 for detecting the presence of an object according to one embodiment.

The method begins at 108, where a non-elastic rigid non-metallic transponder housing 30 containing a transponder 38 is attached to each of one or more rigid surgical implements 14. In addition, in some embodiments, a transponder device 20 may also be carried, attached, or coupled to other surgical implements, such as other rigid implements and non-rigid implements, like sponges or gauze. After attaching the transponder housing 30, at least one of the rigid surgical implements 14 is used to perform the surgery at 110. In some embodiments, some or all of the surgical implements 14 may not be used during surgery. For example, the operating room may have additional surgical implements 14 that are used in case there are complications or surgical implements of various sizes may be present so that the right one can be used for the task at hand.

After the use of the surgical implements 14, a signal is transmitted in a first frequency band at 112. Subsequently, a second signal is transmitted in a second frequency band at 114. A response may be received, if any, to the transmission of the first frequency band at 116. A response may be received, if any, to the transmission of the second frequency band at 118. At 120, based on the responses received, it is determined if a transponder 38 has been detected. If so, the presence of a transponder 38 may be indicated at 122 and if not, the method ends at 124. The presence may be indicated in a number of manners, including but not limited to, visually on a display, lighting up LEDs on the detection/interrogation device, or by emitting a sound. After indicating the presence of the transponder 38, the method ends.

In some embodiments, some of the acts may be performed in different orders. For example, the response to the first frequency band, if any, may be received before the transmission of the second signal in the second signal band. In addition, in one embodiment, one or more of the surgical implements 14 may be sterilized (e.g., by autoclaving) with the attached transponder housing. In other embodiments, the transponder housing 30 may be removed from the surgical implement 14 prior to sterilizing, disposal and/or refurbishing of the surgical implement 14.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other metallic implements, other types of transponders, and other interrogation and detection systems. For instance, the transponder device may be used to mark implements anytime detection of the presence of marked objects is desirable in a confined area, not just during surgery. For example, it may be used to make sure marked tools are not left inside a machine (e.g., vehicle, copy machine) after maintenance is performed. In at least some embodiments, the transponder housing may be utilized to mark objects to determine the removal of a marked implement from a confined area, such as a chef knife from a kitchen of an airport restaurant or computers from a server room. In such an embodiment, an interrogation device, for example, may be placed proximate to a door of the confined area.

In addition, a housing may be manufactured and distributed for tagging objects without a transponder currently attached. Advantageously, the housing can then be used to place a transponder compatible with a particular detection and interrogation system at a subsequent time, including by the end-user.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, if any, including but not limited to U.S. Pat. No. 6,026,818, issued Feb. 22, 2000; U.S. Patent Publication No. US 2004/0250819, published Dec. 16, 2004; U.S. Provisional Patent Application Ser. No. 60/811,376, filed Jun. 6, 2006; and U.S. Provisional Patent Application Ser. No. 60/892,208, filed Feb. 28, 2007 are incorporated herein by reference, in their entirety. Aspects of the embodiments can be modified, if necessary, to employ concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

We claim:

1. A device to mark surgical implements, comprising: a non-elastic rigid housing attachable to a portion of a surgical implement, the housing including a rigid shell having two body portions forming a receiving cavity sized and shaped to closely receive at least a portion of the surgical implement and a transponder receiving cavity within said rigid shell sized to receive a transponder, wherein the rigid shell fixedly spaces the transponder receiving cavity at least about 1 millimeter from any portion of the surgical implement when the housing is attached to the surgical implement.

2. The device of claim 1, further comprising:
the transponder, wherein the transponder is removably retained in the transponder receiving cavity.

3. The device of claim 1 wherein the housing is removably attachable to the portion of the surgical implement.

4. The device of claim 1, further comprising:
a detent mechanism that is integral to the housing to attach the housing to the portion of the surgical implement.

5. The device of claim 1 wherein the implement receiving cavity is an asymmetric passage.

6. The device of claim 1 wherein the rigid shell fixedly spaces the transponder receiving cavity at least about two millimeters from any portion of the surgical implement when the housing is attached to the surgical implement.

7. The device of claim 1 wherein the rigid shell of the housing has a coupling structure adapted to connect the two body portions together.

8. The device of claim 7 wherein the coupling structure is a snap.

9. The device of claim 7 wherein the coupling structure is a clip.

10. The device of claim 7 wherein the two body portions of the shell of the housing are connected by a hinge.

11. The device of claim 10 wherein the hinge is integral with the two body portions.

12. The device of claim 1 wherein the housing is composed of plastic, the plastic able to withstand multiple sterilizations in an autoclave.

13. The device of claim 1 wherein the housing is non-metallic.

14. A transponder device comprising:
a rigid housing having at least two distinct pieces, the housing removably attachable to a portion of a surgical implement by enclosing the portion of the surgical implement within an implement receiving cavity of the housing;
coupling means for coupling the at least two distinct pieces together to form a transponder receiving cavity and the implement receiving cavity therebetween; and
a wireless transponder received in the transponder receiving cavity.

15. The transponder device of claim 14 wherein at least one of the pieces of the housing is non-elastic.

16. The transponder device of claim 14 wherein at least one of the pieces of the housing is non-metallic.

17. The transponder device of claim 14 wherein the rigid housing fixedly spaces the wireless transponder at least about 1 millimeter from the surgical implement when attached to the portion of the surgical implement.

18. The transponder device of claim 17 wherein the rigid housing fixedly spaces the wireless transponder at least about 2 millimeters from the surgical implement when coupled to the surgical implement.

19. The transponder device of claim 14 wherein at least one piece of the housing is made of plastic, the plastic able to withstand multiple sterilizations in an autoclave.

20. The transponder device of claim 14, further comprising:
a detent mechanism that is integral to the housing to attach the housing to the portion of the surgical implement.

21. The transponder device of claim 14 wherein the implement receiving cavity of the housing is an asymmetric passage.

22. A surgical instrument comprising:
instrument means;
a handle connected to the instrument means;
a non-elastic rigid non-metallic housing removably attached to at least a portion of the handle, the housing having a two-piece body coupled together by coupling means to form a transponder receiving cavity and an implement receiving cavity therebetween; and
a wireless transponder enclosed within the transponder receiving cavity of the rigid housing wherein the rigid housing fixedly spaces the wireless transponder at least about 1 millimeter from the handle when the housing is clamped to a portion of the surgical implement with the portion received in the implement receiving cavity.

23. The surgical instrument of claim 22 wherein the instrument means is at least one of a cutting means, a grasping means, a clamping means, an access means, an injection/irrigation means, or a measurement means.

24. The surgical instrument of claim 22 wherein the coupling means is at least one of a snap, a strap, or a clip.

25. The surgical instrument of claim 22 wherein the rigid housing fixedly spaces the wireless transponder at least about 2 millimeters from the at least a portion of the handle.

26. The surgical instrument of claim 22 wherein the housing has an integral detent mechanism to attach the housing to the at least a portion of the handle.

27. The surgical instrument of claim 22 wherein the instrument means is metallic.

* * * * *